United States Patent [19]

Kubein-Meesenburg et al.

[11] Patent Number: 5,336,267
[45] Date of Patent: Aug. 9, 1994

[54] ARTIFICIAL JOINT

[76] Inventors: Dietmar Kubein-Meesenburg, Burgweg 1a, D-3350 Kreiensen; Hans Nägerl, Lange Hecke 41, 3407 Gleichen/OT Klein-Lengden, both of Fed. Rep. of Germany

[21] Appl. No.: 9,439

[22] Filed: Jan. 26, 1993

Related U.S. Application Data

[63] Continuation of Ser. No. 760,604, Sep. 16, 1991, abandoned.

[30] Foreign Application Priority Data

Mar. 18, 1989 [DE] Fed. Rep. of Germany ....... 3908958

[51] Int. Cl.$^5$ .................. A61F 2/32; A61F 2/36; A61F 2/30
[52] U.S. Cl. ........................ 623/22; 623/23; 623/18
[58] Field of Search .............. 623/16, 17, 18, 19, 623/20, 21, 22, 23

[56] References Cited

U.S. PATENT DOCUMENTS

| | | | |
|---|---|---|---|
| Re. 29,757 | 9/1978 | Helfet | 623/20 |
| 3,906,550 | 9/1975 | Rostoker et al. | 623/16 |
| 3,916,451 | 11/1975 | Buechel et al. | |
| 4,003,095 | 1/1977 | Gristina | |
| 4,808,185 | 2/1989 | Penenberg et al. | 623/20 |

FOREIGN PATENT DOCUMENTS

| | | |
|---|---|---|
| 0226762 | 7/1987 | European Pat. Off. |
| 3341723 | 3/1985 | Fed. Rep. of Germany |
| 8704917 | 8/1987 | World Int. Prop. O. |

*Primary Examiner*—Randall L. Green
*Assistant Examiner*—Dinh X. Nguyen
*Attorney, Agent, or Firm*—Jones & Askew

[57] ABSTRACT

Artificial joint for replacing human joints in particular, consisting of at least two joint parts with spherical functional surfaces that can move relative to each other.

The curvature relationships of the functional surfaces having a circular cross-sectional contour are convex/convex, convex/concave or concave/concave relative to each other, and the geometric design of the joint is determined by a joint chain with two joint axes running through the centers of rotation $M_1$ and $M_2$ of the functional surfaces with radii $R_1$ and $R_2$, where $R_1$ is the radius of the circular cross-sectional contour of the functional surface with center of rotation $M_1$, and $R_2$ is the radius of the circular cross-sectional contour of the functional surface with center of rotation $M_2$.

2 Claims, 2 Drawing Sheets

ARTIFICIAL JOINT

This is a continuation of application Ser. No. 07/760,604, filed Sep. 16, 1991, now abandoned.

The present invention concerns an artificial joint for replacing human joints in particular, consisting of at least two joint parts with spherical functional surfaces that move relative to each other.

In any human joint, smooth lubricated functional surfaces slide and roll against each other and their movement is influenced only by minor speed-dependent frictional forces because of the fluid lubrication. If the joint has an especially well-defined direction of operation, then the body part guided by the joint most commonly will execute a planar motion relative to the part that is connected to it and can be regarded as stationary. Around this movement, the general movement range is limited to a relatively narrow angular range in both directions (e.g., with the jaw, knee and other hinge-like joints). It has been found that the known artificial joints do not adequately simulate the functions of a natural joint so they are subject to early wear and lead to impairment for the person who must rely on such joints.

This invention is based on the problem of creating artificial joints with a structure that assures functioning that largely corresponds to that of natural joints and thus yields unimpaired function without complaints for a long period of time when used to replace a human joint.

According to this invention, this is accomplished by the fact that the curvature relationships of the functional surfaces which have a circular contour when seen in cross section are convex/convex, convex/concave or concave/concave relative to each other and the geometric design of the joint is determined by a joint chain through two axes passing through the centers $M_1$ and $M_2$ of rotation of the functional surfaces with radii $R_1$ and $R_2$, where $R_1$ is the radius of the circular cross-sectional contour of the functional surface with the center of rotation $M_1$, and $R_2$ is the radius of the circular cross-sectional contour of the functional surface with the center of rotation $M_2$. This invention is based on the finding that the sliding movement of two spherical functional surfaces against each other can be reduced to the sliding movement of two curves against each other for a planar motion. According to this invention, these two curves are formed by the two cross-sectional contours through the joint surfaces, where double convexity, convexity/concavity and double concavity are the three possible kinematic relationships of joints. The cross-sectional contours according to this invention pass through the force-transmitting areas of the joint surfaces. According to this invention, a joint is thus formed by a "dimeric" joint chain.

According to this invention, it is advantageous when a pressure distributing body is provided, where the surfaces that are in contact with the functional surfaces have a curvature that conforms to that of the functional surfaces. This pressure distributing body is provided between the two functional surfaces, where the thickness D of the pressure distributing body on the line connecting the centers of rotation $M_1$ and $M_2$ depends on the load acting on the joint.

This invention will now be explained in greater detail with reference to the embodiments illustrated in the accompanying figures which show the following:

Figure 1:
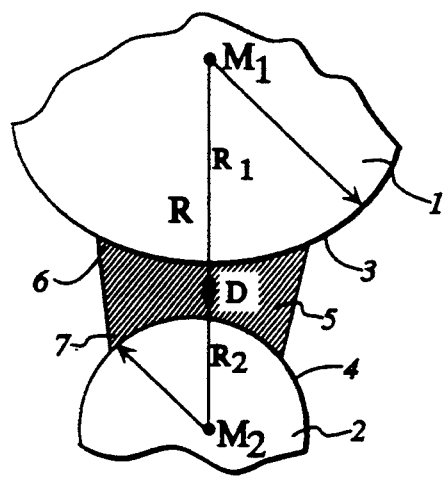
FIG. 1 shows a schematic diagram of the functional surfaces of a joint according to this invention with double convexity.

As FIG. 1 shows, a joint according to this invention consists of joint part 1 and joint part 2. In the embodiment illustrated here, joint parts 1 and 2 each have convex functional surfaces 3 and 4. These functional surfaces 3 and 4 each have a circular cross-sectional contour, and functional surface 1 has center of rotation $M_1$ while functional surface 2 has center of rotation $M_2$. The circular cross-sectional contour of functional surface 1 has radius $R_1$ and the circular cross-sectional contour of functional surface 4 has radius $R_2$. The path of the joint axes of the joint according to this invention has a radius R which is obtained from the following equation $$R = R_1 + R_2 + D$$

where D is the thickness of pressure distributing body 5 on the line connecting the two centers of rotation $M_1$ and $M_2$. Pressure distributing body 5 has friction surfaces 6 and 7, each of which has a curvature adapted to conform to functional surfaces 3 and 4, respectively. The thickness D of pressure distributing body 5 depends on the load in the joint. The radius R of the path of the joint axes is given, i.e., it is determined by the natural joint which is to be replaced by the artificial joint. As an alternative, the radii $R_1$ and $R_2$ can be measured subsequently on the natural joint, which thus means that an artificial joint designed on the basis of a natural joint can be manufactured using the individual parameters. Essentially the radius R is the constant that defines the artificial joint as well as the natural joint. The artificial joint can be produced with radii $R_1$, $R_2$ and D that differ from the natural dimensions, but the sum of radii R remains the same in order to adapt the artificial materials used to make the joint to the conditions of load optimization.

The joint according to this invention is thus designed like a joint chain with two joint axes, i.e., it is a so-called "dimeric" joint chain.

The technical implementation of such a dimeric joint chain corresponds to a design based on two round parts that are held a distance R apart from each other by means of a rod.

Then the two bodies that are joined together in a hinged manner are attached to the moving ends of the joint chain. In the design of the joint according to this invention as illustrated in FIG. 1, it is essential that the two centers of rotation $M_1$ and $M_2$ are each located in their respective joint parts 1 and 2. The purpose of the pressure distributing body 5 is to distribute the forces that occur in the joint over the functional surfaces of the joint in such a way that the contact surfaces are enlarged in order to avoid spot loads.

Figure 2:
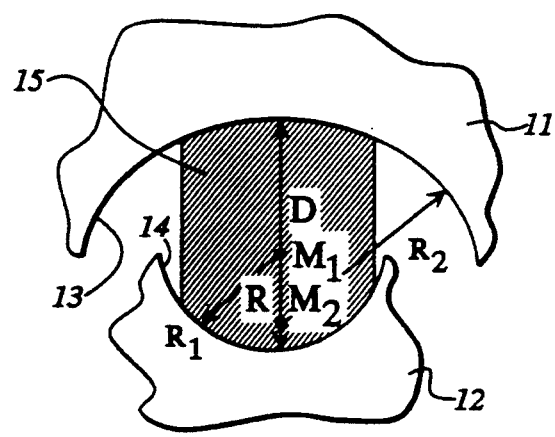
FIG. 2 shows a schematic diagram of the functional surfaces of a joint according to this invention with double concavity.

FIG. 2 illustrates a joint according to this invention that consists of joint parts 11 and 12. These joint parts 11 and 12 have concave functional surfaces 13, 14 with a circular cross-sectional contour, and a pressure distributing body 15 is arranged between joint parts 11 and 12. The radius R of the path of the joint axes of this joint according to this invention is obtained from the following equation $$R = R_2 + R_1 - D$$

where D again indicates the thickness of the pressure distributing body 15 on the line connecting centers of rotation $M_1$ and $M_2$, where the centers of rotation $M_1$ and $M_2$ are within the pressure distributing body. $R_1$ is the radius of the circular cross-sectional contour about the center of rotation $M_1$, and $R_2$ is the radius of the circular cross-sectional contour about the center of rotation $M_2$.

Figure 3:
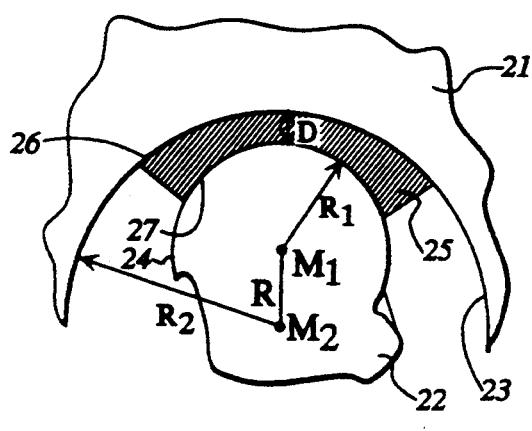
FIGS. 3 and 4 show schematic diagrams of the functional surfaces of a joint according to this invention with convexity/concavity.

FIG. 3 shows another design of a joint according to this invention in a schematic diagram, where the two joint bodies 21 and 22 have different spherical curvatures. Joint body 21 has a concave functional surface 23 and joint body 22 has a convex functional surface 24.

A pressure distributing body 25 is again provided between joint parts 21 and 22. This pressure distributing body has joint surfaces 26 and 27. Joint part 22 has center of rotation $M_1$, and the circular cross-sectional contour of functional surface 24 of joint part 22 has the radius $R_1$. Joint part 21 has center of rotation $M_2$ and its concave functional surface 23 has the radius $R_2$ in its circular cross-sectional contour. The centers of rotation here are located within the joint part with the convex functional surface 24. The radius R of the path of the joint axis is obtained from the equation $$R = R_2 - R_1 - D$$

where D is again the thickness of the pressure distributing body 25 on the line connecting centers of rotation $M_1$ and $M_2$.

Figure 4:
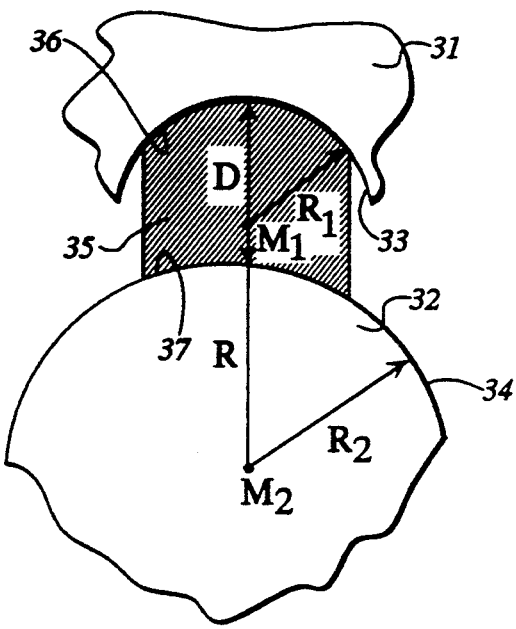

FIG. 4 illustrates an alternative embodiment of a joint according to this invention with joint parts 31 and 32. Here again, one joint part, namely joint part 31, has a concave functional surface 33 and joint part 32 has a convex functional surface 34. In contrast with the embodiment according to FIG. 3, the circular cross-sectional contour of the convex functional surface here has a larger radius, namely radius $R_2$ with the center of rotation $M_2$, and joint part 31 has concave functional surface 33 with a radius $R_1$ that is smaller than that of functional surface 23 and has the center of rotation $M_1$. The centers of rotation are arranged in such a way that the center of rotation of joint part 35 is located within said joint part, and the center of rotation of joint part 31 is located within pressure distributing body 35 which is located between the two joint parts 31 and 32. Pressure distributing body 35 has friction surfaces 36 and 37 that are in contact with functional surfaces 33 and 34. The radius R of the path of the joint axes is obtained from the following equation $$R = R_2 - R_1 + D$$

The path of the joint axes of the individual joints illustrated in FIGS. 1 to 4 is always the path, namely a circular path, with which each center of rotation $M_1$ and $M_2$ moves about the other center of rotation, depending on the respective reference system. These movements of centers of rotation $M_1$ and $M_2$ are independent of the additional rotation of the functional surfaces about their own centers.

Figure 5:
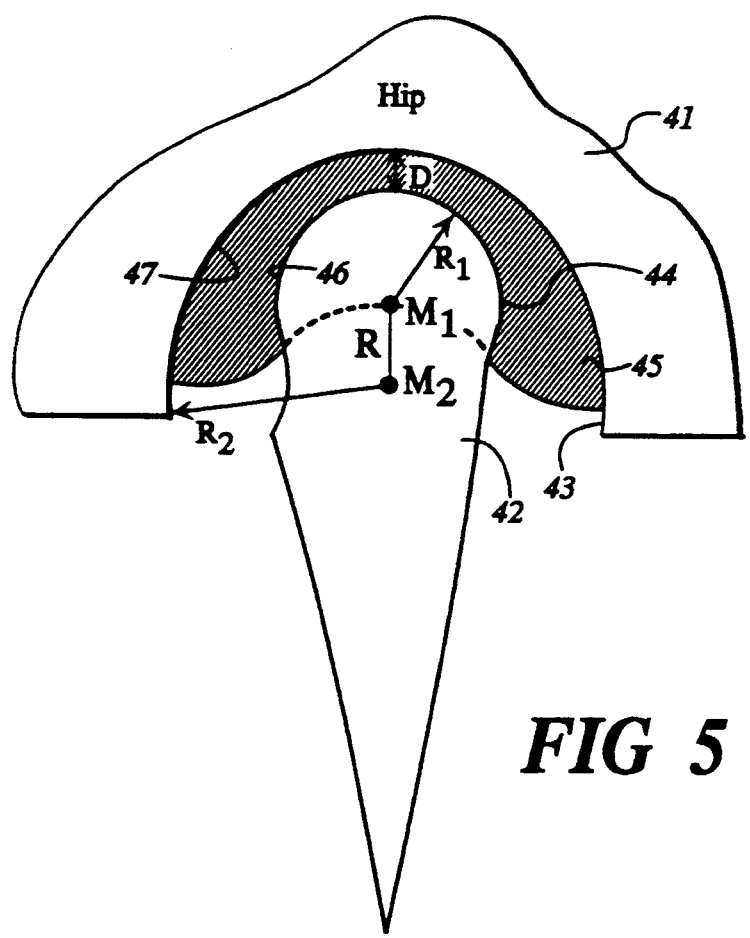
FIG. 5 shows a schematic diagram of a joint according to this invention as a hip joint for use in humans.

FIG. 5 shows the embodiment of a joint according to this invention as a human hip joint which is an application of the joint design according to FIG. 3. In other words, this is a case of convexity/concavity where hip bone 41 has socket 43 as the concave functional surface. The center of rotation of the hip bone or socket is $M_2$ and the radius of the circular functional surface of the socket is $R_2$. The other joint part is formed by femur 42 which has a convex functional surface 44 with center of rotation $M_1$ and radius $R_1$ as the radius of curvature. Pressure distributing body 45 is provided between the two joint parts 41 and 42. Its friction surfaces 45 and 46 are in contact with functional surfaces 43 and 44 and have a curvature that conforms to and matches that of the functional surfaces. It is advantageous that the design of pressure distributing body 45 is such that it extends beyond the center of the hemispherical part of femur 42 so the joint according to this invention as illustrated here can also withstand a certain amount of tension and cannot fall apart, e.g., due to the force of gravity on the leg or the calf. This is also true with respect to the outer friction surface 47 of pressure distributing body 45 which also extends over half of the hemispherical functional surface 43.

One measure provided according to this invention is that this locking of the joint by means of the pressure distributing body into the cavity formed by functional surface 43 need not occur at all points around the curvature.

Figure 6:
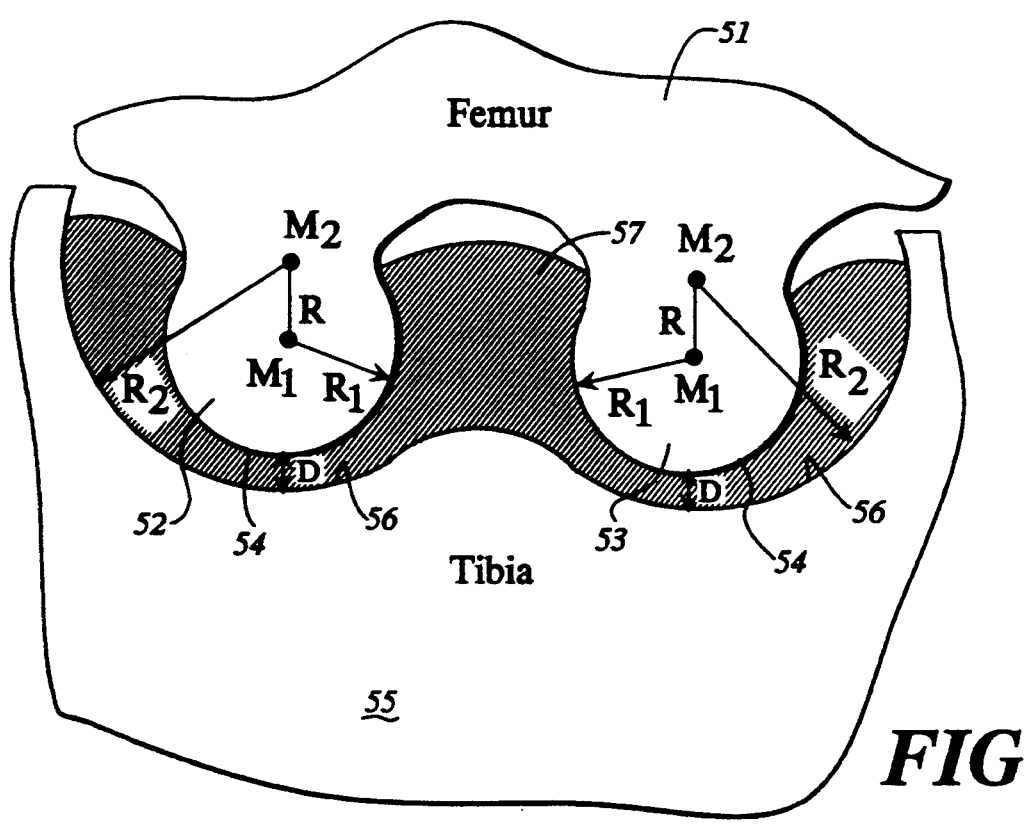
FIG. 6 shows a schematic diagram of a joint according to this invention as a knee joint.

FIG. 6 shows the external design of a joint system such as that required to simulate the human knee joint. This joint system consists of a parallel connection of two joints according to this invention that conform to the joint design in FIG. 3, where femur 51 is provided with two joint parts 52 and 53 that are arranged parallel to each other and each part has a convex functional surface 54. Convex functional surfaces 54 have a center of rotation $M_1$ and a radius $R_1$ of their circular cross-sectional contour. In the tibia, there are two functional surfaces 56 arranged parallel to each other and with a concavity such that their center of rotation $M_2$ is located inside femur 51. These functional surfaces 56 each have a circular cross-sectional contour with the radius $R_2$. A pressure distributing body 57 is provided between the functional surfaces or joint parts 51, 55. This pressure distributing body is designed in such a way that its friction surfaces 58 and 59 are each extended over half of the hemispherical functional surfaces of joint parts 51 and 55 so that joint parts 51 and 55 are clamped in position.

Furthermore, it is possible according to this invention to provide a series connection of such joints to form a joint system in addition to using the parallel connection of individual joint forms according to FIGS. 1 to 4.

We claim:

1. An artificial joint for replacing human joints and comprising:
   at least two joint elements (21, 22; 41, 42; 51, 55) with moving spherical functional surfaces (23, 24; 43, 44; 54, 56);
   the curvatures of the functional surfaces (23, 24; 43, 44; 54, 56) being circular in cross section and being convex-concave and having a first and a second center of rotation ($M_1$, $M_2$) within the joint element (22; 42; 52, 53) with the convex functional surface (24; 44; 54);

a pressure distribution element having a predetermined thickness, the pressure distribution element being (25; 45; 57) slideably located between the two functional surfaces and having opposed sliding surfaces (26, 27; 46, 47; 56) that articulate with the functional surfaces (23, 24; 43, 44; 54, 56) and having a correspondingly curved configuration, with the path of movement of the joint being determined by two joint axes passing through the centers of rotations ($M_1$, $M_2$) of the functional surfaces (23, 24; 43, 44; 54, 56) with the radii ($R_1$, $R_2$), where $R_1$ is the radius of the circular cross-sectional contour of the functional surface (24; 44; 54) with the first center of rotation ($M_1$) and $R_2$ is the radius of the circular cross-sectional contour of the functional surface (23; 43; 56) with the second center of rotation ($M_2$); and wherein the thickness (D) of the pressure distribution element (25; 45; 57) on a line connecting the centers of rotation ($M_1$, $M_2$) is such that the joint axes of the centers or rotation ($M_1$, $M_2$) move on a path having a radius $R = R_2 - R_1 - D$, so that the first center of rotation ($M_1$) is between the pressure distribution element and the second center of rotation ($M_2$).

2. An artificial joint as in claim 1, wherein $R_2 > R_1$.

* * * * *

UNITED STATES PATENT AND TRADEMARK OFFICE
CERTIFICATE OF CORRECTION

PATENT NO. : 5,336,267
DATED : August 9, 1994
INVENTOR(S) : Dietmar Kubein-Messenburg, et. al.

It is certified that error appears in the above-indentified patent and that said Letters Patent is hereby corrected as shown below:

Column 6, line 8, change "or" to --of--.

Signed and Sealed this

Eleventh Day of October, 1994

Attest:

BRUCE LEHMAN

Attesting Officer     Commissioner of Patents and Trademarks